US006821549B2

(12) United States Patent
Jayaraman

(10) Patent No.: US 6,821,549 B2
(45) Date of Patent: Nov. 23, 2004

(54) PROCESS FOR COATING A SURFACE OF A STENT

(75) Inventor: Swaminathan Jayaraman, Fremont, CA (US)

(73) Assignee: Vascular Concept Holdings Limited (GB)

( * ) Notice: Subject to any disclaimer, the term of this patent is extended or adjusted under 35 U.S.C. 154(b) by 29 days.

(21) Appl. No.: 10/320,795

(22) Filed: Dec. 16, 2002

(65) Prior Publication Data

US 2003/0099765 A1 May 29, 2003

Related U.S. Application Data

(63) Continuation-in-part of application No. 09/994,256, filed on Nov. 26, 2001, now Pat. No. 6,517,889.

(51) Int. Cl.[7] ............................ A61L 27/00; B05D 1/18; B05D 1/40

(52) U.S. Cl. .................. 427/2.24; 427/2.1; 427/2.25; 427/2.28; 427/2.3; 427/355; 427/235; 427/232; 427/430.1; 427/230; 427/231; 427/233; 427/234; 427/421; 427/425

(58) Field of Search ............................ 427/2.24, 2.25, 427/2.28, 2.3, 355, 235, 232, 430.1, 2.1, 230, 231, 233, 234, 421, 425

(56) References Cited

U.S. PATENT DOCUMENTS

| 5,282,785 A | 2/1994 | Shapland et al. |
|---|---|---|
| 5,286,254 A | 2/1994 | Shapland et al. |
| 5,460,859 A | 10/1995 | Reale |
| 5,837,313 A | 11/1998 | Ding et al. |
| 5,891,507 A | 4/1999 | Jayaraman |
| 5,902,317 A | 5/1999 | Kleshinski et al. |
| 5,997,468 A | 12/1999 | Wolff et al. |
| 6,071,305 A | 6/2000 | Brown et al. |
| 6,129,705 A | 10/2000 | Grantz |
| 6,143,037 A | 11/2000 | Goldstein et al. |
| 6,153,252 A | 11/2000 | Hossainy et al. |
| 6,203,551 B1 | 3/2001 | Wu |
| 6,214,115 B1 | 4/2001 | Taylor et al. |
| 6,231,600 B1 | 5/2001 | Zhong |
| 6,238,430 B1 | 5/2001 | Klumb et al. |
| 6,248,127 B1 | 6/2001 | Shah et al. |
| 6,251,136 B1 | 6/2001 | Guruwaiya et al. |
| 6,254,634 B1 | 7/2001 | Anderson et al. |
| 6,258,121 B1 | 7/2001 | Yang et al. |
| 6,273,913 B1 | 8/2001 | Wright et al. |
| 6,305,436 B1 | 10/2001 | Andersen et al. |
| 6,335,029 B1 | 1/2002 | Kamath et al. |
| 6,368,658 B1 | 4/2002 | Schwarz et al. |
| 2001/0027340 A1 | 10/2001 | Wright et al. |
| 2003/0215564 A1 * | 11/2003 | Heller et al. ............... 427/2.25 |

FOREIGN PATENT DOCUMENTS

WO    WO 98/55162 A2    12/1998

OTHER PUBLICATIONS

Reddy, KR, Controlled–Release, Pegylation, Liposomal Formulations: New Mechanisms in the Delivery of Injectable Drugs, The Annals of Pharmacotherapy, vol. 34, pp 915–923, Jul./Aug. 2000.

* cited by examiner

Primary Examiner—Jennifer Kolb Michener
(74) Attorney, Agent, or Firm—Fleit Kain Gibbons Gutman Bongini & Bianco; Paul D. Bianco; Martin Fleit

(57) ABSTRACT

The invention relates to a method of coating a surface of a stent by contacting the stent with a coating solution containing a coating material, inserting a thread through the lumen of the stent, and producing relative motion between the stent and the thread to substantially remove coating material located within the openings of the stent. Eliminating or minimizing coating material located within the openings preserves the functionality of the stent. The method can be used to apply a primer layer, a polymer, either with or without a therapeutic agent, and/or a top layer on the stent.

44 Claims, 3 Drawing Sheets

PROCESS FOR COATING A SURFACE OF A STENT

CROSS REFERENCE TO RELATED APPLICATIONS

This application is a continuation-in-part of U.S. patent application Ser. No. 09/994,256, filed Nov. 26, 2001 now U.S. Pat. No. 6,517,889.

FIELD OF THE INVENTION

The present invention relates to a process for coating an implant, and in particular to a process for coating a surface of a stent.

BACKGROUND OF THE INVENTION

A stent is typically an open tubular structure that has a pattern (or patterns) of apertures extending from the outer surface of the stent to the lumen. It is commonplace to make stents of biocompatible metallic materials, with the patterns cut on the surface with a laser machine. The stent can be electro-polished to minimize surface irregularities since these irregularities can trigger an adverse biological response. However, stents may still stimulate foreign body reactions that result in thrombosis or restenosis. To avoid these complications, a variety of stent coatings and compositions have been proposed in the prior art literature both to reduce the incidence of these complications or other complications and restore tissue function by itself or by delivering therapeutic compound to the lumen. Difficulties in coating stents, especially electro-polished stents include the following:

1. The surface of the electro-polished stent is extremely smooth and has a mirror like surface. It is very difficult for materials to bond to this surface. These materials may include polymers, drugs, polymers encapsulated with drugs, etc.

2. The patterns or designs on the surface of the stent have several gaps or ridges in between them and while coating the surface with materials, these materials will usually fill the holes between the struts or the walls of the stent. Expansion of the stent after implantation may cause on unpredictable release of the coating agent inside the vessel wall.

3. It is desirable to have a very thin coating of material on the stent otherwise during expansion of the stent these materials will delaminate or flake off producing undesirable results.

The prior art literature discloses a number of processes and techniques that attempt to solve these and other difficulties associated with stent coating. The generally followed methods of coating stents are dip coating, spray coating, and chemical bonding.

Stents are coated by simple dip coating with a polymer or a polymer and pharmaceutical/therapeutic agents. Dip coating is usually the most successful for low viscosity coatings. The presence of pharmaceutical agents in polymers usually makes the coating solutions more viscous because they need to encapsulate the drug. Dip coating using high viscosity solutions typically causes bridging, i.e. forming of a film across the open space between structural members of the device. This bridging can interfere with the mechanical performance of the stent, such as expansion during deployment in a vessel lumen. Bridges tend to delaminate and rupture during expansion and provide sites that activate platelet deposition by creating flow disturbances in the adjacent hemodynamic environment. In addition, delamination may cause particles to dislodge from the stent surface, potentially leading to other complications. Multiple dip coatings only increase the above phenomenon and also restrict sustained release.

During a spray coating process, micro-sized spray particles are deposited on top of the stent. Particles are lost due to the atomization process and this loss also results in the loss of significant amounts of the pharmaceutical agents, which can be quite costly. In order to load the stent with a maximum drug profile for active release it is desirable to not lose as much particles as possible in the polymer matrix.

Several bonding techniques, such as anionic bonding and cationic bonding, can also be used for attaching the polymers and the encapsulated polymers on the surface of the stent. During the anionic bonding process, the polymer is applied to the surface where the bonding between the pharmaceutical agent and the polymer is a chemical mixture rather than a strong bond. In covalent bonding, the attachment of the polymer and the pharmaceutical mixture to the surface of the stent is through a chemical reaction. For example, the stent is first cleaned with a primer that leaves a hydroxyl-terminated group on the surface of the stent. This hydroxyl-terminated group attaches itself to the polymer chain, which in turn contains the pharmaceutical compound chemically attached to it. In these chemical bonding techniques, there is still a need to avoid bridging between the struts of the stent.

A number of patents have issued that attempt to address these shortcomings. For example, U.S. Pat. No. 6,273,913 issued to Wright et al. describes a stent in which rapamycin is delivered locally, particularly from an intravascular stent, directly from micropores in the stent body or mixed or bound to a polymer coating applied on the stent, to inhibit neointimal tissue proliferation and thereby prevent restenosis.

U.S. Pat. No. 6,258,121 issued to Yang et al. discusses a stent having a polymeric coating for controllably releasing an included active agent. The polymeric coating includes a blend of a first polymeric material, which if alone, would release the agent at a first, higher rate, and a second polymeric material, which if alone would release the agent at a second, lower rate over a longer time period. One stent coating utilizes a faster releasing hydrophilic polymeric material and a slower releasing hydrophobic material.

U.S. Pat. No. 6,251,136 issued to Guruwaiya et al. describes a pharmacological agent that is applied to a stent in dry, micronized form over a sticky base coating. A membrane forming polymer, selected for its ability to allow the diffusion of the pharmacological agent therethrough, is applied over the entire stent. More specifically, a stent, typically a metal stent has a layer of sticky material applied to selected surfaces of the stent. A pharmacological agent is layered on the sticky material and a membrane forming a polymer coating is applied over the pharmacological agent. The membrane is formed from a polymer that permits diffusion of the pharmacological agent over a predetermined time period.

U.S. Pat. No. 6,248,127 issued to Shah et al. describes coatings in which biopolymers may be covalently linked to a substrate. Such biopolymers include those that impart thrombo-resistance and/or biocompatibility to the substrate, which may be a medical device. The disclosed coatings include those that permit coating of a medical device in a single layer, including coatings that permit applying the single layer without a primer.

U.S. Pat. No. 6,231,600 issued to Zhong describes a device, such as a stent, which is provided with a hybrid coating that includes a time released, restenosis inhibiting coating and a nonthrombogenic coating to prevent clotting on the device. One first coat or layer includes a polymer, a cross linking agent, and pacitaxel, analogues, or derivatives thereof. A stent can be provided with a first coat including an aqueous dispersion or emulsion of a polymer and an excess of cross linking agent. The first coating can be dried, leaving a water insoluble polymer coating. A second aqueous coating including a solution or dispersion of heparin can be applied over the first coating, the heparin becoming covalently bound to the cross linking agent on the first coating surface.

U.S. Pat. No. 6,203,551 issued to Wu describes a chamber that allows a user to medicate an implantable prosthesis such as a stent. The implantable prosthesis is capable of securing a therapeutic substance and subsequently delivering the therapeutic substance to local tissues. The chamber allows a user to medicate the prosthesis subsequent to the sterilization process and immediately prior to the implantation procedure. The chamber includes a prosthesis crimped on a balloon of a catheter assembly. A user can supply therapeutic substances into the chamber and allow the therapeutic substances to be secured by the prosthesis. After allowing the prosthesis to be soaked by the therapeutic substances for a predetermined amount of time, the chamber is removed and the prosthesis is ready for the implantation procedure.

U.S. Pat. No. 6,153,252 issued to Hossainy et al. describes a process that attempts to avoid bridging. The stent is contacted with a liquid coating solution containing a film forming biocompatible polymer under conditions suitable to allow the film forming biocompatible polymer to coat at least one surface of the stent while maintaining a fluid flow through the passages sufficient to prevent the film forming biocompatible polymer from substantially blocking the passages. The patent also described stents coated by this process.

U.S. Pat. No. 6,071,305 issued to Brown et al. relates to a directional drug delivery stent that includes an elongated or tubular member having a cavity containing a biologically active agent. In one embodiment, the active agent is diffused from the reservoir directly to the walls of a body lumen, such as a blood vessel, through directional delivery openings arranged on an outer surface of the elongated member. Another variation of the stent includes an osmotic engine assembly for controlling the delivery of the active agent from the reservoir.

U.S. Pat. No. 5,891,507 issued to Jayaraman describes a process whereby the stent is dipped inside a bath of the coating material. The stent oscillates inside the bath with application of external energy. Ultrasonic energy is usually applied externally, which permits the rotation and vibration of the stent while it is immersed in the medium.

U.S. Pat. No. 5,837,313 issued to Ding et al. describes a method of coating an open lattice metallic stent prosthesis which includes sequentially applying a plurality of relatively thin outer layers of a coating composition comprising a solvent mixture of uncured polymeric silicone material and cross linked and finely divided biologically active species to form a coating on each stent surface. The coatings are cured in situ and the coated, cured prosthesis are sterilized in a step that includes preferred pretreatment with argon gas plasma and exposure to gamma radiation electron beam, ethylene oxide, or steam.

Published U.S. patent application Ser. No. US2001/ 0027340 describes delivery of rapamycin locally, particularly from an intravascular stent, directly from micropores in the stent body or mixed or bound to a polymer coating applied on stent, to inhibit neointimal tissue proliferation and thereby prevent restenosis.

In spite of this prior art, a need still exists for an improved process for coating a surface of a stent.

SUMMARY OF THE INVENTION

Stents typically have a lumen, inner and outer surfaces, and openings extending from the outer surface to the inner surface. The present invention relates to a method for coating a surface of a stent. At least a portion of the stent is placed in contact with a coating solution containing a coating material to be deposited on the surface of the stent. A thread is inserted through the lumen of the stent, and relative motion between the stent and the thread is produced to substantially remove coating material within the openings.

The thread can have a diameter substantially smaller than the diameter of the lumen. The thread can be inserted through the lumen either after or prior to contacting the stent with the coating solution. Relative motion between the stent and the thread can be produced prior to contacting the stent with the coating solution to clean the stent. The thread can be either a filament or a cable with a plurality of wires. The thread can be made of a metallic or polymeric material.

The stent can be dipped into the coating solution or spray coated with the coating solution. The coating material can include a biocompatible polymer, either with or without a pharmaceutically active compound.

In one embodiment, the relative motion is oscillatory motion produced by a vibrating device. The oscillations can be changed (magnitude and/or frequency) to vary thickness of the coating solution on the stent. In another embodiment, the relative motion is produced by a shaker table. Regardless of the type of motion, the relative motion can be produced either after or while the stent is in contact with the coating solution.

The relative motion between the stent and the thread can include initially moving the stent in a horizontal direction substantially parallel to the length of the thread and subsequently moving the stent in a vertical direction substantially perpendicular to the length of the thread. The movement in the horizontal direction can be repeated, with pauses between repetitions. The movement in the vertical direction can also be repeated, with the horizontal and vertical movements alternating.

In order to smooth the relative motion, the thread can be coupled to a damping compensator. The damping compensator connects the thread to a vibrating device. In one embodiment, the damping compensator comprises first and second filaments connected to the thread.

The relative motion can be motion of the stent along the thread. For example, a first end of the thread can be attached to a first stand at a first height and a second end of the thread is attached to a second stand at a second height. The relative motion is produced by a gravity gradient, with the first height differing from the second height. Furthermore, the stent can be moved back and forth between the first and second stands by sequentially increasing or decreasing at least one of the first and second heights. In this way, multiple coatings can be applied to the stent.

The relative motion can also be rotation of the stent relative to the thread. A stream of gas can be passed along at least a portion of the surface of the stent to rotate the stent relative to the thread. The rotation can also occur in conjunction with other relative motion between the stent and the thread.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE EMBODIMENTS

Figure 1:
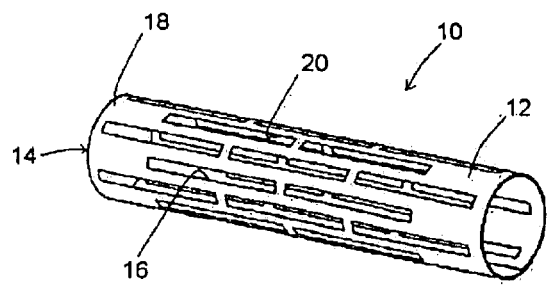
FIG. 1 shows a perspective view of a stent.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto. Finally, any reference to a particular biological application, such as use of a stent for cardiovascular applications, is simply used for convenience as one example of a possible use for the invention and is not intended to limit the scope of the present invention thereto.

As previously noted, stents are provided with openings because such openings are instrumental in expanding the stent and facilitating the retention of a stent in its position of placement within the body. The openings allow tissues to grow and/or protrude therethrough to facilitate firm fixation of an implanted stent. Obscuring or covering of the stent openings during a coating process creates a great risk of failure of a stent implantation operation.

Accordingly, the present invention relates to a method for coating a stent with a coating material without obscuring the openings of the stent. The method can be used with stents having openings in any form, such as slits, slots, ovoid, circular or the like shape. The stents may also be composed of helically wound or serpentine wire structures in which the spaces between the wires form the openings. Stents may be flat perforated structures that are subsequently rolled to form tubular structures or cylindrical structures that are woven, wrapped, drilled, etched or cut to form openings.

Figure 2:
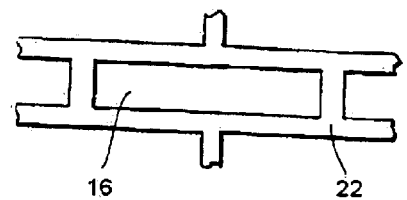
FIG. 2 shows an enlarged view of a portion of the stent of FIG. 1.

FIG. 1 shows one example of a stent 10 that can be coated with the method according to the present invention. Stent 10 includes a generally tubular body 12 with a lumen 14. A plurality of openings 16 extends from an outer surface 18 to an inner surface 20. FIG. 2 shows a close up view of the openings 16, which are defined by struts or bridges 22 of material.

Stent 10 can be made of any suitable biocompatible materials, including biostable and bioabsorbable materials. Suitable biocompatible metallic materials include, but are not limited to, stainless steel, tantalum, titanium alloys (including nitinol), and cobalt alloys (including cobalt-chromium-nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, $\epsilon$-caprolactone, etc. and blends thereof).

Figure 3:
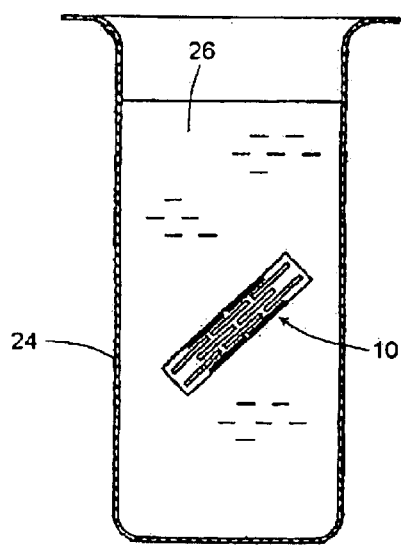
FIG. 3 shows a bath that contains a stent immersed in a coating solution.

According to the method of the present invention, at least a portion of a surface of stent 10, i.e. part or all of outer and/or inner surfaces 18, 20 of struts 22, can be coated with a film of coating material without having significant amounts of coating material located within openings 16. In order to achieve this, at least a portion of stent 10 is placed in contact with a coating solution containing a coating material to be deposited on the desired surface or surfaces of stent 10. As shown in FIG. 3, stent 10 is dipped or immersed in a container 24 containing coating solution 26. Alternatively, stent 10 can be sprayed with the coating solution. Other suitable means for containing stent 10 with the coating solution can also be used.

The coating material in the coating solution can be a primer, i.e. a layer or film of material upon which another coating is applied, a polymer either with or without a pharmaceutically active compound, or an overcoat, i.e. a layer or film of material placed over another coating. Non-limited examples of coating materials are described below.

Figure 4:
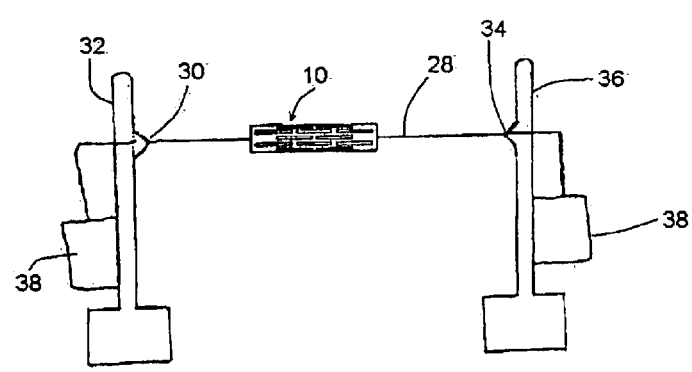
FIG. 4 shows a stent mounted on a thread running between two stands, with each stand having a vibration-producing device such that motion is produced on both sides of the thread.

Either before or after contacting stent 10 with the coating solution, stent 10 is mounted on a thread. Specifically, and as shown in FIG. 4, a thread 28 is inserted through lumen 14 of stent 10. The diameter of thread 28 is substantially smaller than the diameter of lumen 14 so that stent 10 can freely move freely with respect to thread 28. Thread 28 can be a single filament or a plurality of filaments, such as a cable with multi-strand wires. Regardless of the nature, thread 28 can be made of a metallic or polymeric material. Metallic materials would include stainless steel wires and the polymeric material could be similar to a suture.

Relative motion between stent 10 and thread 28 is produced (either manually or automated) to substantially remove any coating material that is located within openings 16. If stent 10 is mounted on thread 28 prior to contact with coating solution, relative motion between stent 10 and thread 28 can be produced prior to contacting stent 10 with the coating solution. This process cleans stent 10 by removing debris or excess material on stent 10. The relative motion can be any type of motion, either of thread 28, stent 10, or both, that would result in removal or shaking off of coating solution or material from openings 16. Examples include oscillatory motion, shaking motion, and simple linear motion.

FIG. 4 shows one arrangement capable of producing relative motion between stent 10 and thread 28. A first end 30 of thread 28 is connected or attached to a first stand 32 and a second end 34 of thread 28 is connected or attached to a second stand 36. As shown in FIG. 4, a vibration device 38 is coupled to each of first and second stands 32, 36. However, a single vibrating producing device could be used. Furthermore, any type of mechanism that generates motion could be used. Examples include servo motors, oscillatory motors, rotational motors, etc. Upon activation of vibration device 38, thread 28 vibrates in a substantially uniform manner to shake off coating solution located within openings 16.

In one embodiment, the relative motion occurs initially in the horizontal direction, i.e. in a direction substantially parallel to the length of thread 28. The horizontal motion can assist in straightening the thread and/or stent. Additionally, this motion can also aid in removing excess coating material that may be sticking to the thread and/or stent. The horizontal motion can occur once or multiple times. If the horizontal motion is repeated, there can be a pause between the repetitions. Once the horizontal motion is completed, vertical motion (i.e. motion in a direction substantially perpendicular to the length of thread 28) can commence. Alternatively, vertical and horizontal motion can be alternated. As described in more detail below, the vertical and horizontal motion can be supplemented with rotational movement of the stent.

Regardless of the type of relative motion, the relative motion between stent 10 and thread 28 can occur either during or after contact of stent 10 with the coating solution. If the relative motion occurs after contact, the relative motion should occur prior to drying of the coating solution. However, removal of coating solution within openings 16 may occur even after the coating solution has dried. Furthermore, the nature of the relative motion, i.e. magnitude, duration, and repetitive frequency, can be varied to vary the thickness of the coating solution on stent 10. For example, if oscillatory motion were used, slower oscillations would produce a thicker film. Conversely, a thin film can be produced by faster oscillations.

Figure 5:
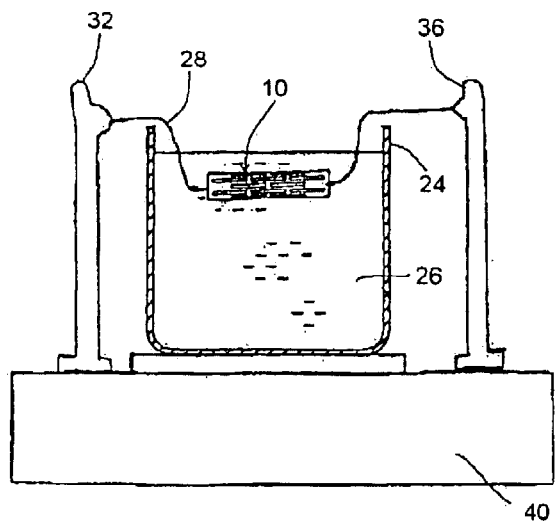
FIG. 5 shows a stent mounted on a thread running between two stands, with the stent dipped in a coating solution. The arrangement is located on a shaker table to provide motion of the stent along the thread. The motion may occur either during or after immersion of the stent in the solution.

FIG. 5 shows another arrangement with stent 10 dipped or immersed into container 24 containing coating solution 26. The entire arrangement is located on a shaker table 40, which is used to produce relative motion between stent 10 and thread 28.

Figure 6:
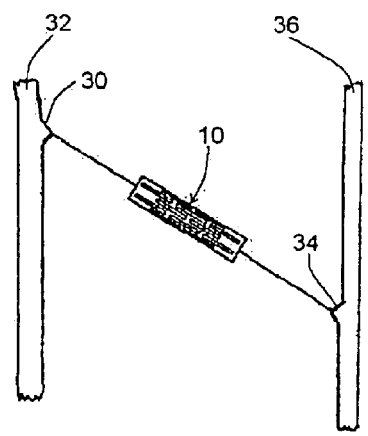
FIG. 6 shows a stent mounted on a thread wherein motion of the stent along the thread from one end of the thread to the other is produced by a gravity gradient.

Instead of oscillating or vibrating stent 10, thread 28 can be positioned so that a gravity gradient exists between first and second ends 30, 34. As shown in FIG. 6, first end 30 of thread 28 is located at a first height and second end 34 of thread 28 is located at a second height. The gravity gradient causes stent 10 to move along thread 28, thereby removing coating solution located within openings 16. Stent 20 can be moved back and forth between first and second ends 30, 34 by increasing or decreasing at least one of the first and second heights. This can be repeated any number of times until a thin film can be formed on the surface. Once the relative movement is completed, stent 10 can be dipped into the coating solution again and the process can be repeated.

Figure 7:
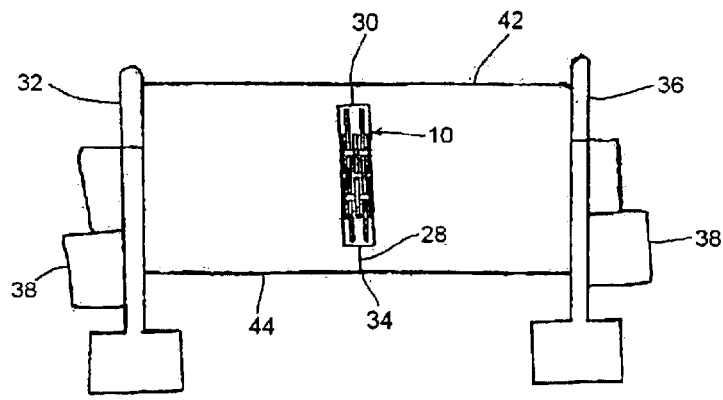
FIG. 7 shows a stent mounted on a thread that is coupled to a vibration-producing device by two other threads.

FIG. 7 shows another arrangement capable of producing relative motion between stent 10 and thread 28. First end 30 of thread 28 is connected or attached to a first filament 42 and second end 34 of thread 28 is connected or attached to a second filament 44. First and second filaments 42, 44 can be threads, as previously defined, or some other elongate member, such as a spring. One end of each of first and second filaments 42, 44 is connected or attached to a first stand 32 and the other end is connected or attached to second stand 34. As shown in FIG. 7, a vibration device 38 is coupled to each of first and second stands 32, 36. However, a single vibrating producing device could be used. Furthermore, any type of mechanism that generates motion could be used. Examples include servo motors, oscillatory motors, rotational motors, etc. Upon activation of vibration device 38, thread 28 vibrates in a substantially uniform manner to shake off coating solution located within openings 16.

In the embodiments shown in FIGS. 4–6, thread 28 was directly coupled to the motion-producing device. Thus, the movement was applied directly to thread 28. In contrast, the embodiment of FIG. 7 involves direct application of movement to first and second filaments 42, 44, which in turn causes movement of thread 28. Thus, the movement is applied indirectly to thread 28. In any motion, there is some amount of damping that is involved before predictable and cyclical motion is produced. In the case of applying motion indirectly (FIG. 7), the damping effect is minimized to create a much smoother motion to thread 28, and thereby stent 10. Smoother motion helps to ensure a more uniform coating is applied to stent 10.

Figure 8:
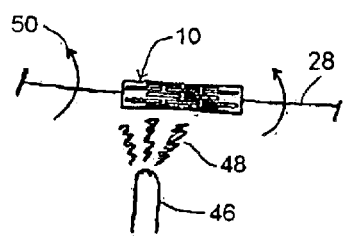
FIG. 8 shows a stent mounted on a thread with a stream of gas applied to the stent to cause the stent to rotate on the thread.

FIG. 8 shows another arrangement capable of producing relative motion between stent 10 and thread 28. As previously noted, stent 10 can be placed on thread 28 either before or after contacting stent 10 with the coating solution. A nozzle 46 is positioned so that when a gas 48 is blown from nozzle 46, stent 10 rotates in the direction of arrow 50. In one embodiment, the rotational movement is used alone and substantially removes any coating material that is located within openings 16. In another embodiment, the rotational movement is used in conjunction with other type of movement (before, after, and/or during) and assists in the removal.

Regardless of whether the rotational movement is used alone or with other movement, the stream of gas can also be used to assist in drying the coating material on stent 10. In this regard, gas 48 can be heated. Gas 48 can be simply compressed air or some other type of gas. One example is argon gas, which is known to be relatively inert. As shown, nozzle 46 is a single nozzle that provides a stream of gas 48 that extends along the length of stent 10. Alternatively, nozzle 46 can be moved, either manually or automatically, along the length of stent 10 so that gas 48 contacts most, if not all, of the surface area of stent 10. In another embodiment, multiple nozzles 46 can be used as the source of gas 48.

Figure 9:
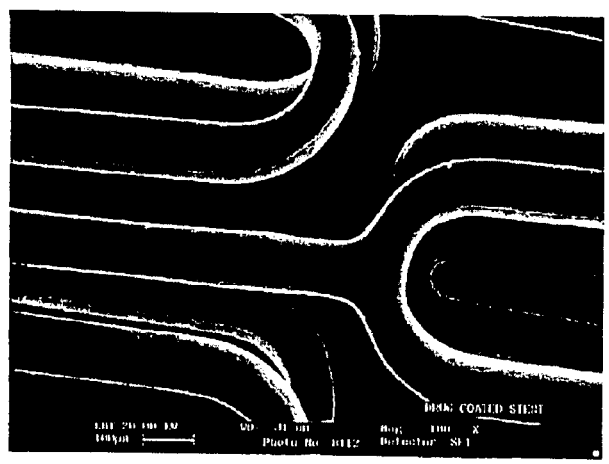
FIG. 9 shows a scanning electron micrograph of a portion of a stent coated according to the present invention.
Figure 10:
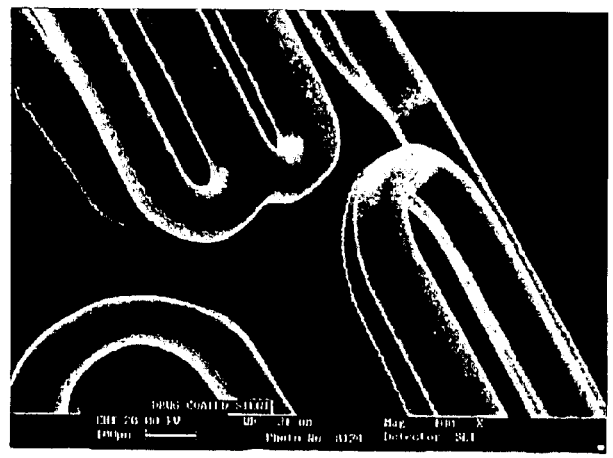
FIG. 10 shows a scanning electron micrograph of a portion of a stent coated according to the present invention.
Figure 11:
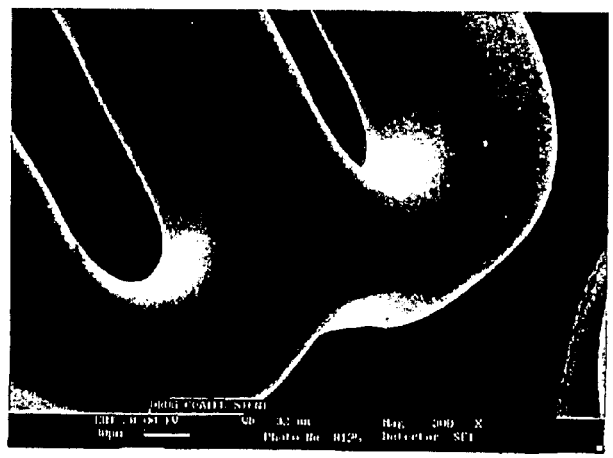
FIG. 11 shows a higher magnification scanning electron micrograph of a section of the stent shown in FIG. 10.

As the micrographs of FIGS. 9–11 illustrate, the method according to the present invention results in a substantially uniform coating without any bridging of coating material within the openings. Film forming polymers that can be used for coatings in this application can be either absorbable or non-absorbable, and should be biocompatible to minimize irritation of any tissue the film may contact. The polymer may be either biostable or bioabsorbable depending on the desired rate of release or the desired degree of polymer stability, but in certain applications, a bioabsorbable polymer may be preferred since, unlike biostable polymer, absorbable polymers will not be present long after implantation to cause any adverse, chronic local response. Biodegradable or bioabsorbable polymers also do not present the risk that over extended periods of time there could be an adhesion loss between the stent and coating caused by the stresses of the biological environment that could dislodge the coating and introduce further problems even after tissue encapsulation of the stent.

Suitable polymers that can be used include, but are not limited to, the following: aliphatic polyesters, poly amino acids, copoly (etheresters), polyalkylenes, polyoxalates, polyamides, polyiminocarbonates, polyorthoesters, polyoxaesters, polyamidoesters, polyoxaesters, polyanhydrides, polyphosphasenes, polylactic acid, polyglycolic acid, poly caprolactones, poly hydroxybutyrate, poly hydroxyvalerate, poly para dioxanone, trimethlene carbonate, polyiminocarbonate, polyurethanes, polymethacrylates, silicones, polyethylene oxide, polyvinylalcohols, polyethylene glycols, polyvinyl pyrrolidone, hydrogels, polyolefins, polyisobutylene, poly acrylics, polyvinyl chloride, polyvinyl methyl ether, poly styrene, poly ethylene-methyl methacrylate, polyacrylonitrile-styrene, ABS resins, ethylene-vinyl acetate, nylon 66, poly carbonates, epoxy resins, rayon, rayon-triacetate, cellulose, cellulose acetate, cellulose acetate butyrate, cellophane, cellulose nitrate, cellulose propionate, cellulose ethers, and polymer blends thereof.

All the above polymers generally have one or more of the below mentioned characteristics:
moderate viscosity
high molecular weight
do not form tacky films upon curing
good adhesion properties
not rubbed off or displaced when the stents are crimped
do not crack during expansion of the stent
high elongation properties
go into solvents easily
solvents can be evaporated either at room temperature or in an oven when the relative
motion takes place.

After the coating process is completed, one or more of the polymers described above may be used to produce a top coat on top of the stent which encapsulates fully the stent, polymeric media with the therapeutic agent.

The following are non-limiting examples of therapeutic agents that can be used in the polymeric mixture: taxol and its derivatives, Vinblastine, vincristine and other vinca alkaloids, macrocyclic antibiotics, other antibiotics, antiproliferative agents, antimitotic agents, anticancer agents, platinum coordination complexes, anticoagulants, antiplatelet agents, antimigratory agents, antisecretory agents, IL 2 inhibitory agents, corticosteroids, anti-inflammatory agents, immunosuppresive agents, angiogenic agents, growth factor inhibitors, and mixtures thereof.

The amount of therapeutic agent will depend on a number of factors, which include, but are not limited to, the particular drug employed, the combination of drugs employed and the medical condition being treated, severity of the condition, location of the condition and also the surface area available for delivery.

The delivery of the therapeutic agent will depend on many factors. These factors include, but are not limited to:

Total area of the stent available whether it is a small diameter application or a larger diameter application. The larger the diameter of the stent, the greater is the surface area and hence more amounts of drugs can be trapped on to the surface of the stent.

The amount of polymer and the amount of drug that is used in the matrix. The determining factor is the release profile of the drug that is desired. It may be desired to release the entire drug within 30 days, or it may be tailored for long term release. For long term release, top coat can be applied so that the blood particles first have to break down the top coat, thereby providing time for the drug to be released into the blood stream subsequent to that. The drug can also be diffused out of the top coat layer. The top coat layer provides a diffusion barrier layer for slow effective release of the drug.

While various descriptions of the present invention are described above, it should be understood that the various features could be used singly or in any combination thereof. Therefore, this invention is not to be limited to only the specifically preferred embodiments depicted herein.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method for coating a surface of a stent having a lumen with a diameter, inner and outer surfaces, and openings extending from the outer surface to the inner surface comprising the steps of:
    contacting at least a portion of the stent with a coating solution containing a coating material to be deposited on the surface of the stent;
    inserting a thread through the lumen of the stent; and
    producing relative motion between the stent and the thread, wherein the relative motion substantially removes coating material within the openings and wherein the thread is coupled to a damping compensator to smooth the relative motion.

2. The method of claim 1 wherein the thread has a diameter and the lumen diameter is at least twice as large as the thread diameter.

3. The method of claim 1 wherein the thread is inserted through the lumen prior to contacting the stent with the coating solution.

4. The method of claim 3 further comprising the step of producing relative motion between the stent and the thread prior to contacting the stent with the coating solution to remove debris from the stent.

5. The method of claim 1 wherein the stent is contacted with the coating solution by dipping the stent into the coating solution.

6. The method of claim 1 wherein the stent is contacted with the coating solution by spraying the coating solution on the stent.

7. The method of claim 1 wherein the coating material includes a biocompatible polymer.

8. The method of claim 7 wherein the coating material further includes a pharmaceutically active compound.

9. The method of claim 1 wherein the relative motion is oscillatory motion.

10. The method of claim 9 wherein the relative motion is produced by a vibrating device.

11. The method of claim 9 wherein the oscillations are changed to vary thickness of the coating solution on the stent.

12. The method of claim 1 wherein the relative motion is produced by a shaker table.

13. The method of claim 1 wherein the relative motion is produced after the stent is contacted with the coating solution.

14. The method of claim 1 wherein the relative motion is produced while the stent is in contact with the coating solution.

15. The method of claim 1 further comprising the steps of drying the stent and applying a second coating.

16. The method of claim 1 wherein the damping compensator connects the thread to a vibrating device.

17. The method of claim 16 wherein the damping compensator comprises first and second filaments connected to the thread.

18. The method of claim 1 further comprising the step of rotating the stent relative to the thread.

19. The method of claim 18 wherein a stream of gas is passed along at least a portion of the surface of the stent to rotate the stent relative to the thread.

20. The method of claim 1 wherein the relative motion is rotation of the stent with respect to the thread.

21. The method of claim 20 wherein a stream of gas is passed along at least a portion of the surface of the stent to rotate the stent relative to the thread.

22. A method for coating a surface of a stent having a lumen with a diameter, inner and outer surfaces, and openings extending from the outer surface to the inner surface comprising the steps of:

contacting at least a portion of the stent with a coating solution containing a coating material to be deposited on the surface of the stent;

inserting a thread through the lumen of the stent; and producing relative motion between the stent and the thread, wherein the relative motion substantially removes coating material within the openings and wherein the step of producing relative motion between the stent and the thread includes initially moving the stent in a horizontal direction substantially parallel to the length of the thread and subsequently moving the stent in a vertical direction substantially perpendicular to the length of the thread.

23. The method of claim 22 wherein the thread has a diameter and the lumen diameter is at least twice as large as the thread diameter.

24. The method of claim 22 wherein the thread is inserted through the lumen prior to contacting the stent with the coating solution.

25. The method of claim 24 further comprising the step of producing relative motion between the stent and the thread prior to contacting the stent with the coating solution to remove debris from the stent.

26. The method of claim 22 wherein the stent is contacted with the coating solution by dipping the stent into the coating solution.

27. The method of claim 22 wherein the stent is contacted with the coating solution by spraying the coating solution on the stent.

28. The method of claim 22 wherein the coating material includes a biocompatible polymer.

29. The method of claim 28 wherein the coating material further includes a pharmaceutically active compound.

30. The method of claim 22 wherein the relative motion is oscillatory motion.

31. The method of claim 30 wherein the relative motion is produced by a vibrating device.

32. The method of claim 26 wherein the oscillations are changed to vary thickness of the coating solution on the stent.

33. The method of claim 22 wherein the relative motion is produced by a shaker table.

34. The method of claim 22 wherein the relative motion is produced after the stent is contacted with the coating solution.

35. The method of claim 22 wherein the relative motion is produced while the stent is in contact with the coating solution.

36. The method of claim 22 further comprising the steps of drying the stent and applying a second coating.

37. The method of claim 22 wherein the movement in the horizontal direction is repeated.

38. The method of claim 37 further comprising the step of pausing between repetitions.

39. The method of claim 37 wherein the movement in the vertical direction is repeated.

40. The method of claim 39 wherein the horizontal and vertical movements are alternated.

41. The method of claim 22 further comprising the step of rotating the stent relative to the thread.

42. The method of claim 41 wherein a stream of gas is passed along at least a portion of the surface of the stent to rotate the stent relative to the thread.

43. The method of claim 22 wherein the relative motion is rotation of the stent with respect to the thread.

44. The method of claim 43 wherein a stream of gas is passed along at least a portion of the surface of the stent to rotate the stent relative to the thread.

* * * * *